(12) United States Patent
Gladnick et al.

(10) Patent No.: US 7,127,159 B2
(45) Date of Patent: Oct. 24, 2006

(54) STROBE ILLUMINATION

(75) Inventors: Paul G. Gladnick, Seattle, WA (US); Richard Wasserman, Kirkland, WA (US)

(73) Assignee: Mitutoyo Corporation, Kawasaki (JP)

( * ) Notice: Subject to any disclaimer, the term of this patent is extended or adjusted under 35 U.S.C. 154(b) by 144 days.

(21) Appl. No.: 10/901,355

(22) Filed: Jul. 29, 2004

(65) Prior Publication Data

US 2006/0024040 A1    Feb. 2, 2006

(51) Int. Cl.
*G03B 15/02* (2006.01)
*H04N 7/18* (2006.01)

(52) U.S. Cl. .................. 396/4; 396/182; 348/132
(58) Field of Classification Search .................. 396/4, 396/164, 182; 362/11, 12; 348/131, 132
See application file for complete search history.

(56) References Cited

U.S. PATENT DOCUMENTS 6,207,946 B1 * 3/2001 Jusoh et al. ............. 250/208.1
6,749,310 B1 * 6/2004 Pohlert et al. ................ 362/11

* cited by examiner

*Primary Examiner*—W. B. Perkey
(74) *Attorney, Agent, or Firm*—Oliff & Berridge, PLC

(57) ABSTRACT

An illumination technique is provided that adjusts the respective light intensities of each of a plurality of light sources that are strobed at desirable consistent intensities by adjusting a respective light pulse pattern for each respective light source. All the light sources are controlled to illuminate an object throughout a strobe duration period. The light pulse patterns may be micro-strobed light pulse patterns, formed by a variety of methods. The illumination technique is usable to preserve the general shape of the edge intensity profile on an object, and allow precision edge position measurements, regardless of whether the object is moving or not during image acquisition.

16 Claims, 11 Drawing Sheets

STROBE ILLUMINATION

BACKGROUND OF THE INVENTION

1. Field of Invention

This invention is directed to strobe illumination.

2. Description of Related Art

Imaging systems are widely used to inspect workpieces as they are transported through a manufacturing process. Equipment such as machine vision inspection systems often capture images of the workpieces using a camera, for example, and process the captured images to verify various workpiece dimensions by identifying edges of relevant features in the images.

The location where an edge is detected within an array of image data is highly dependent on lighting of the workpiece during image capture. Edge artifacts or edge-shifting may be created by lighting-specific shadows cast due to improper illumination of the workpiece. To increase productivity, workpieces are often kept in motion even during image capture. This places an additional burden on illumination systems to minimize blurring caused by the motion. Such factors frequently limit the accuracy with which the edge of a feature can be located within an image and/or the velocity that can be tolerated during image capture. Thus, improvements in workpiece illumination technology are very desirable.

SUMMARY OF THE DISCLOSURE

Strobe lighting may be used to minimize blurring caused by workpiece motion during image capture. A short strobe duration produces a workpiece motion "freezing" effect and a camera may capture one image per strobe, for example. Light sources illuminating a workpiece may be operated at their maximum allowable intensities so that camera CCD integration times, or at least the effective image exposure times as determined by the lighting, may be minimized. However, typically, not all light sources of an illumination system can be operated at their maximum intensities because, as noted above, edge artifacts or edge-shifting may be created by improper illumination of the workpiece. Improper illumination of the workpiece may include an improper mixture of light intensities from various light sources that are used to illuminate the workpiece. Thus, a proper mixture of light intensities must be maintained to reduce (if not eliminate) artifacts.

Unfortunately, operating light sources at less than their maximum intensities may introduce undesirable light source behavior. For example, it is more difficult to strobe a light source at a particular intensity intermediate between zero and a maximum intensity. Further, other light source characteristics, such as the emitted frequency spectrum, may change depending on their operating intensity. Optical systems that are used in connection with inspection systems often have a significant frequency sensitivity, particularly in relation to the nominal accuracies of some precision machine vision inspection systems. Thus, variations in spectrum output may cause undesirable artifacts, imaging errors, and/or measurement errors.

Additionally, the workpiece motion "freezing" accomplished by strobe lighting becomes increasingly imperfect at higher workpiece movement speeds, and at longer strobe durations. This is particularly significant when edge locations are to be determined with refined levels of subpixel precision within an image. Moreover, in many applications, it is desirable to attain, as closely as possible, the same edge location measurement from a strobed image that would be obtained from an image of a workpiece that is not moving relative to the imaging system. Thus, given a practical minimum time for strobe durations and a trend toward ever higher workpiece speeds, it is desirable to implement strobe lighting in such a way that it is possible to compensate for any residual edge-shifting due to any residual blur in a strobed image.

In view of these circumstances, a workpiece illumination technique is provided to adjust the respective time-averaged light intensity of respective light sources by adjusting the light pulse pattern of respective light sources that are strobed between two controllable intensities, such as strobing the light sources between on and off states, for example.

In accordance with one aspect of the invention, all the light sources are controlled to illuminate the workpiece in a uniform manner throughout each strobe duration period. To achieve the proper mixture of time-averaged light intensities of the various light sources throughout a strobe duration period, the light intensities of the light sources are controlled by micro-strobing, which controls the respective time-averaged intensity of each respective light source.

In accordance with a further aspect of the invention, the time-averaged intensity of each respective light source is controlled by setting a respective micro-strobing light pulse pattern.

In accordance with a further aspect of the invention, the micro-strobing light pulse pattern of each respective light source is uniform throughout the strobe duration period.

In accordance with a further aspect of the invention, the micro-strobing light pulse pattern is set by setting a respective micro-strobing duty cycle.

In accordance with a further aspect of the invention, the micro-strobing light pulse pattern is set by setting a respective micro-strobing repetition rate that is used in conjunction with a prescribed pulse duration.

In accordance with another aspect of the invention, during an image exposure, a respective time-averaged light intensity is desired from each of the various light sources. A strobe duration period is governed by using a respective maximum density light pulse pattern to operate the respective light source from which the highest respective time-averaged light intensity is desired. The other respective light sources are then operated using respectively lower density light pulse patterns, in order to provide their respective desired time-averaged light intensities over that same strobe duration period.

In accordance with a further aspect of the invention, the time-averaged light intensity of each respective light source is approximately constant throughout that same strobe duration period.

In accordance with another aspect of the invention, during an image exposure, a respective overall illumination energy is desired from each of the various light sources. A minimum strobe duration period is governed by using a respective maximum density light pulse pattern to operate the respective light source from which the highest respective overall illumination energy is desired. The other respective light sources are then operated at respectively lower density light pulse patterns, to distribute their respective overall illumination energies over that same strobe duration period.

In accordance with a further aspect of the invention, the overall illumination energy of each respective light source is distributed in a respective uniform manner throughout that same strobe duration period.

In accordance with another aspect of the invention, a time equal to a proportion of the strobe duration period is used in conjunction with an operative workpiece velocity during a strobed image in order to compensate a latched position value associated with an image. The latched position value is used in conjunction with a blurred edge location within that image to determine an overall measured coordinate value of the corresponding edge on the workpiece.

BRIEF DESCRIPTION OF THE DRAWINGS

Various exemplary embodiments are described in detail, with reference to the following figures, wherein.

DETAILED DESCRIPTION OF EXEMPLARY EMBODIMENTS

Figure 1:
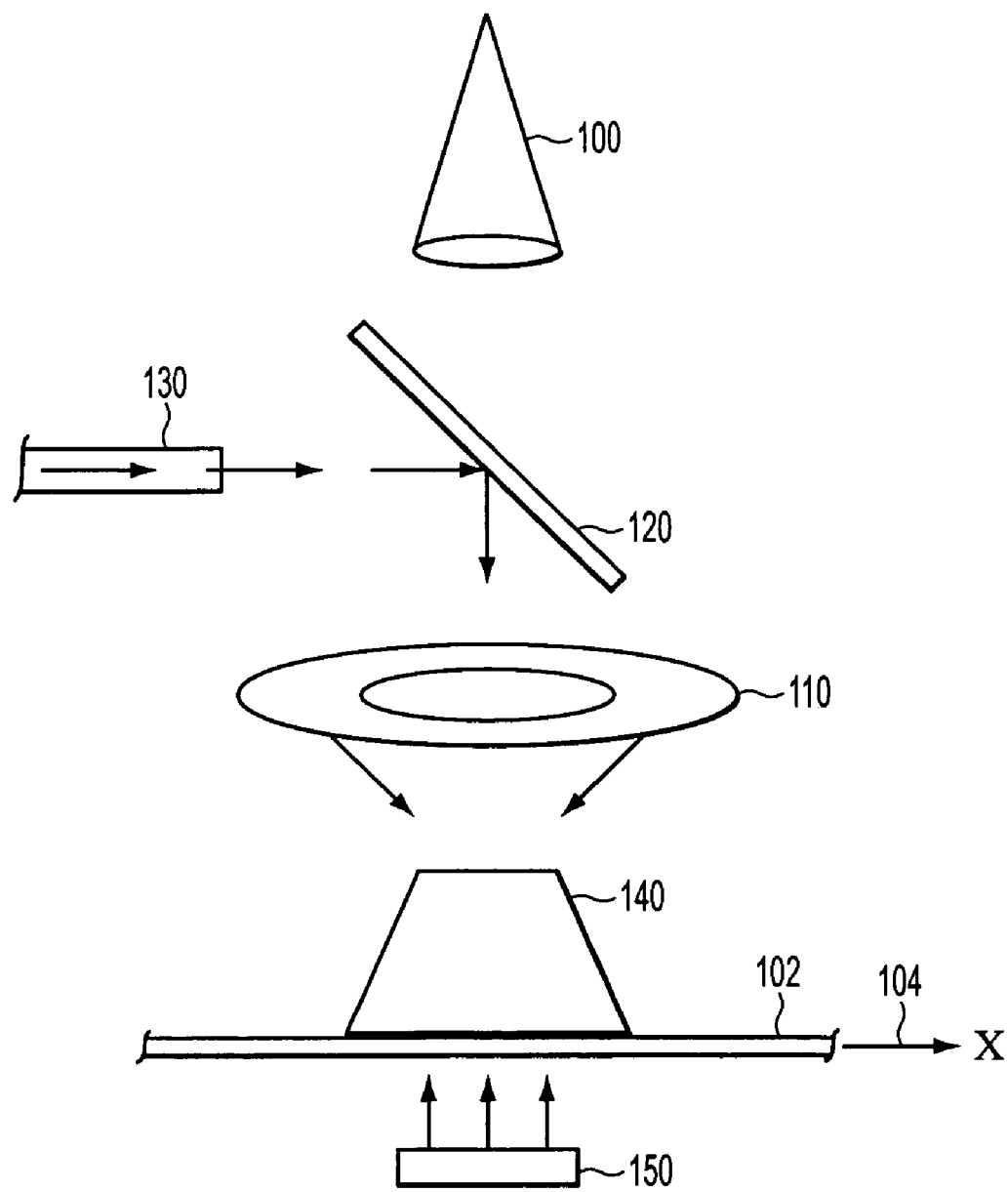
FIG. 1 shows an exemplary diagram of a lighting system.

Micro-strobing may be applied to any machine vision illumination system to achieve desirable, accuracy-enhancing, lighting characteristics. For example, FIG. 1 shows an exemplary lighting system in which the micro-strobing technique may be applied. A workpiece 140 is placed on a moving mechanism such as a transparent stage 102, for example. The transparent stage 102 may comprise a transparent portion of an X-Y stage, a transparent conveyor belt, or the like. A stage light 150, a ring light 110 and a coaxial light 130 together with a half-silvered turning mirror 120 illuminate the workpiece 140. A photodetector 100, such as the CV-A1-20 CCD camera, manufactured by JAI of Copenhagen, Denmark, captures the light reflected from the workpiece 140 to form an image in the form of an array of pixels, for example, that may be processed to identify and inspect relevant features of the workpiece 140. For purposes of explanation, a nominal direction of motion 104, of the workpiece relative illumination and imaging components, is shown along an x-axis in FIG. 1.

Figure 2:
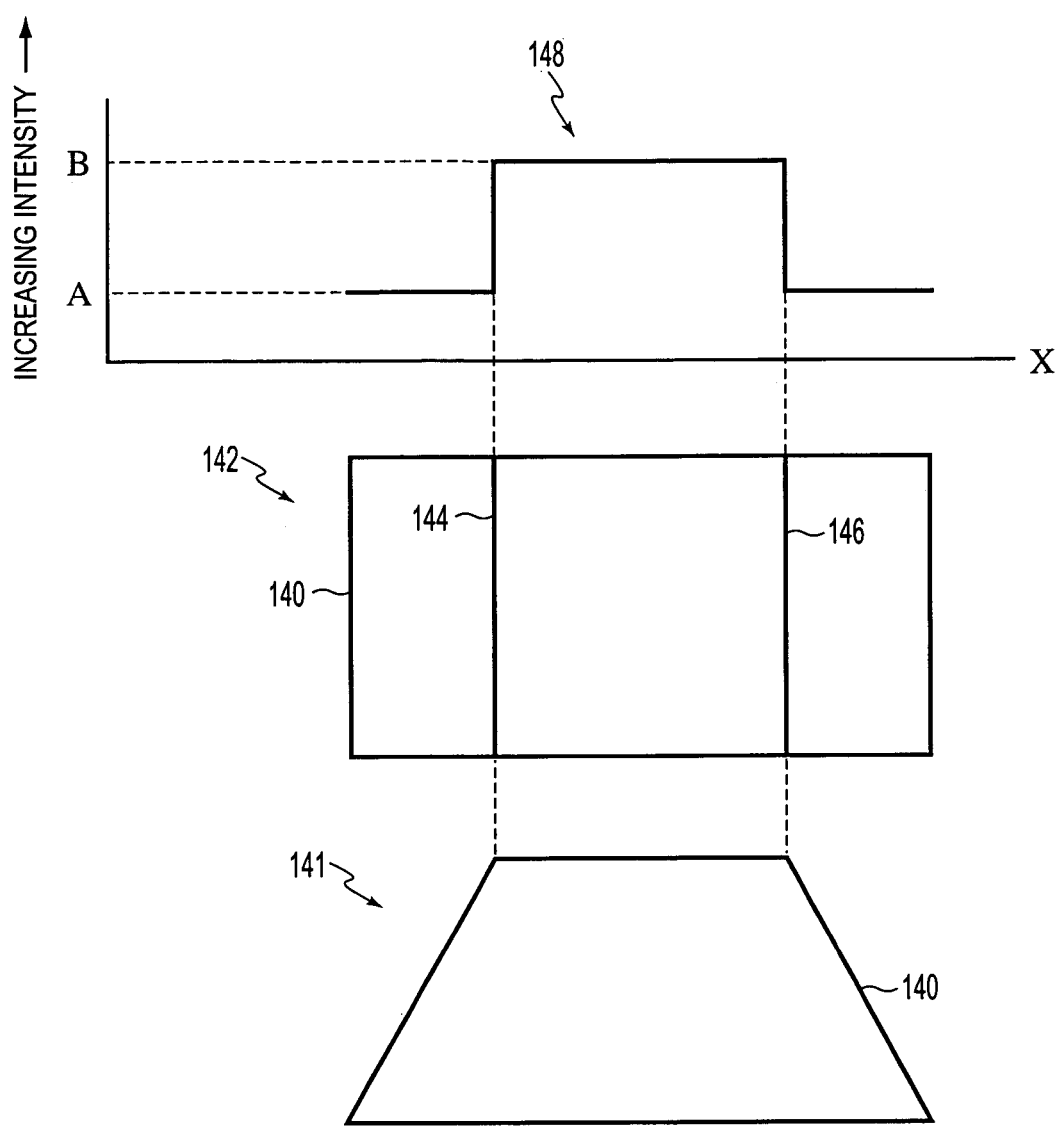
FIG. 2 illustrates a top view of an exemplary workpiece as may be viewed by a photodetector and a corresponding light intensity profile.

FIG. 2 shows a side view 141 and a top view 142 of the workpiece 140. In this figure the top view 142 depicts at least two edges 144 and 146 formed by the top corners of the workpiece 140 which run along the width of an opaque trapezoidal block. In this example, light generated by ring light 110 and coaxial light 130 is reflected, or diffusely reflected, towards the photodetector 100 by the top and angled side surfaces of workpiece 140, while the light emitted by stage light 150 is blocked by workpiece 140. The light intensity detected by photodetector 100 has a nominal intensity profile 148 along the x-axis direction which shows edges 144 and 146 as intensity steps between intensity levels A and B. For example, if photodetector 100 is a CCD array having rows oriented along the x-axis direction and the motion direction 104 shown in FIG. 2, then the pixels that image the areas located to the left of edge 144 and to the right of edge 146 receive lower light intensities than the pixels that image the area between edges 144 and 146.

Figure 3:
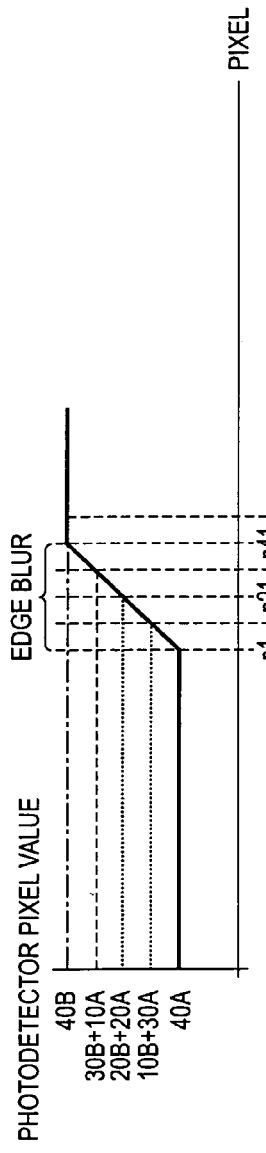
FIGS. 3–5 illustrate blur effects of workpiece motion.
Figure 4:
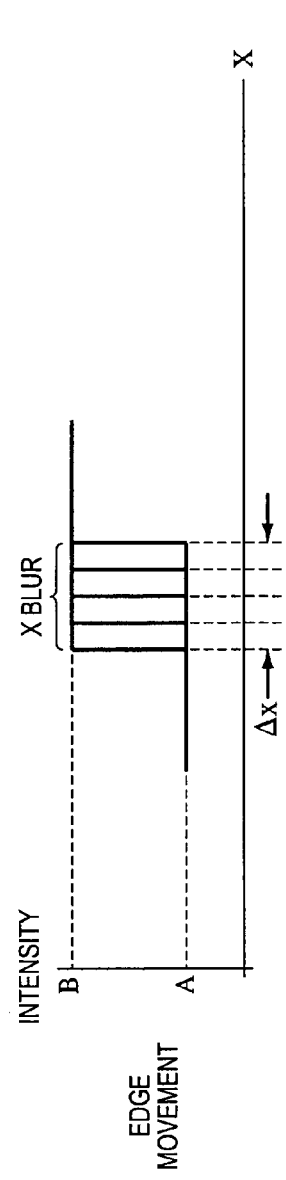
Figure 5:
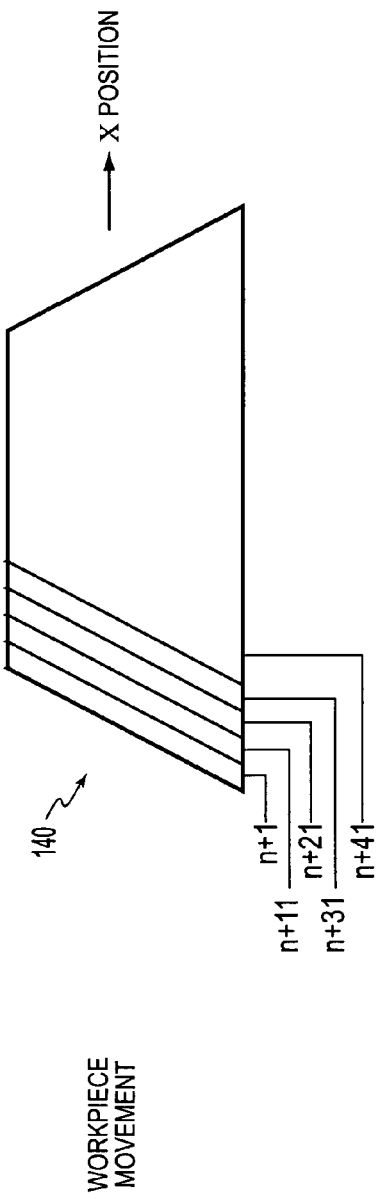

As indicated above, workpiece 140 is moved along motion direction 104 by stage 102 during image capture causing an intensity profile differing from the intensity profile 148 to be received by the photodetector 100. During movement of the stage 102, edges 144 and 146 are swept across the photodetector 100 causing a blurring effect. FIGS. 3–5 show an exemplary blurring effect on the image of edge 144, due to motion during an effective exposure time. FIG. 5 shows workpiece 140 being moved along the x-axis between exposure time increments n+1 to n+41 at a constant velocity. However, for purposes of discussion, time and spatial increments are used. Assume for simplicity of discussion that the incremental movement distance of workpiece 140 along the x-axis for each time increment corresponds to one pixel of the photodetector 100 (e.g., photodetector 100 includes a two-dimensional array of pixels). FIG. 5 shows the position of workpiece 40 corresponding to time increments n+1, n+11, n+21, n+31 and n+41.

FIG. 4 shows the left edge of the intensity profile 148 of FIG. 2 corresponding to each of the time increments n+1, n+11, ... n+41. Thus, edge 144 moves a distance $\Delta x$ along the x-axis causing a blur if photodetector 100 integrates the light over an exposure time interval (integration time) between n+1 and n+41 time increments.

FIG. 3 shows light accumulation or integration values output by adjacent pixels designated p1–p51 of photodetector 100. The photodetector 100 accumulates charges generated by incident light. Thus, light accumulation is represented by an amount of charge accumulated in a pixel. Photodetectors are reset at the beginning of an integration time and accumulate (integrate) charges as an indication of an amount of light detected. Thus, the graph in FIG. 3 represents the light accumulation or integration values of each of the pixels. Such values are alternatively referred to as photodetector pixel intensity values, light accumulation values, or gray level values.

At time n+1, the pixel designated p1 initially receives light intensity B reflected from the top surface of workpiece 140. However, the light intensity immediately drops to light intensity A due to the motion. The light intensity illuminating the pixel p1 remains at A for the remainder of the photodetector integration time, leading to an accumulated pixel intensity value that can be represented by a relative value of approximately 40 A.

At pixel p11, the light intensity remains at B during time increment n+1 to time increment n+11 and drops to A thereafter. Thus, the accumulated pixel intensity value at pixel p11 can be represented by a relative value of approximately 10B+30 A. At pixel p21, the light intensity remains at B for the first 20 time increments from n+1 through n+21 and drops to A thereafter. Thus, the light accumulation value at pixel p21 can be represented by a relative value of approximately 20B+20 A. For similar reasons as discussed above in connection with pixels p11 and p21, pixel p31 has a relative light accumulation value of approximately 30B+10 A and pixel p41 has a relative light accumulation value of approximately 40 B.

The light accumulation value at pixel p51 is the same as that for pixel p41 because the light intensity value remained at B for the total integration time of the photodetector 100. Thus, instead of edge 144 forming a step between pixels p1 and p11, it is spread across pixels p1–p41. According to this simple example, the amount of light accumulated in these pixels forms a line with constant slope (assuming that workpiece 140 is moving at a constant velocity). Thus, the sharp edge represented by an ideal intensity step in FIG. 2 is captured as a blurred edge represented by increasing light accumulation values between pixels p1 and p41 in FIG. 3.

As noted above, the workpiece motion "freezing" accomplished by strobe lighting is increasingly imperfect at higher workpiece speeds, and at longer strobe durations. Conversely, workpiece motion freezing may be improved by faster strobe lighting or slower workpiece speeds, so that edges such as edge 144 may be sharpened, and thus more precisely located in an image, by reducing the number of pixels affected by the edge movement. However, it should be appreciated that in various precision machine vision inspection systems image edges are routinely located with repeatability better than 1/10 of a pixel, and often on the order of 1/100 of a pixel, by known methods of sub-pixel interpolation. Thus, even when blurring is limited to a range of less than one pixel, image edges are "blurred" and/or improperly located at a sub-pixel level due to slight alterations in the gray level value of adjacent pixels due to workpiece motion during the effective exposure time. In some applications, a workpiece speed of at least 10 mm/sec is desirable. In such a case, in order to provide blurring corresponding to at most 1 micron, an overall strobe duration period of at most 100 microseconds is desirable. Of course, for faster speeds, or smaller amounts of blur, an overall strobe duration period that is as short as possible is desirable.

Figure 6:
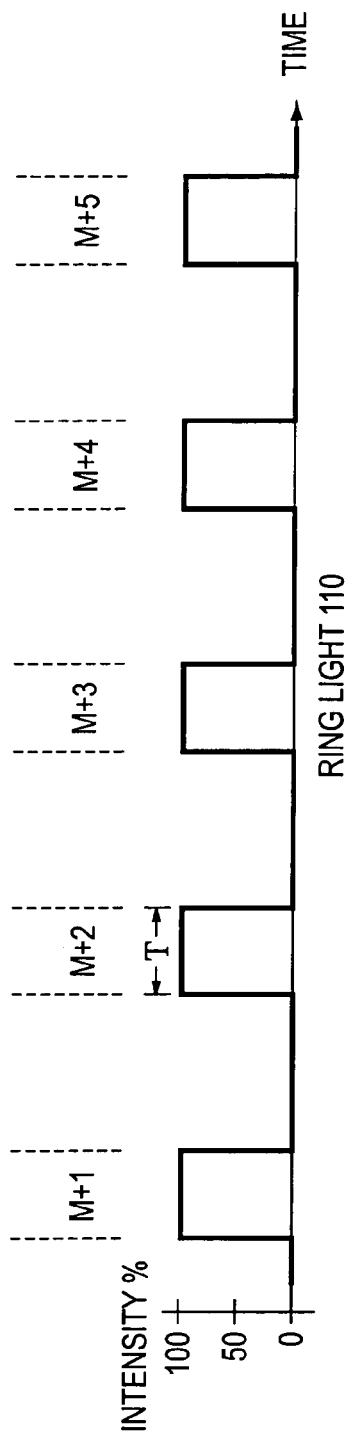
FIGS. 6–8 illustrate an exemplary strobe lighting.
Figure 7:
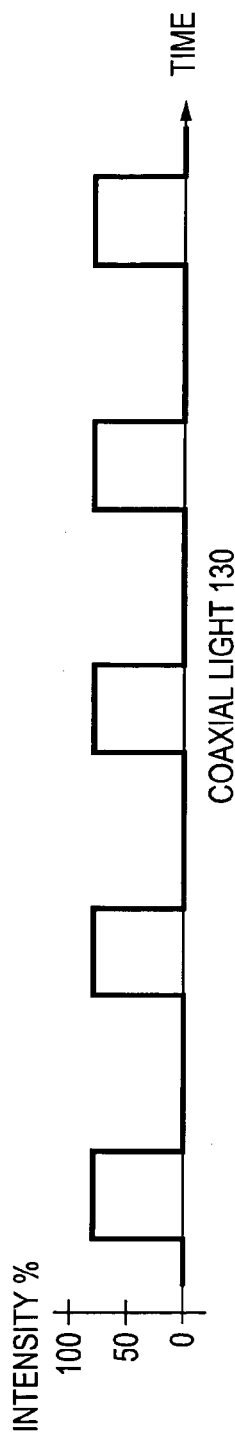
Figure 8:
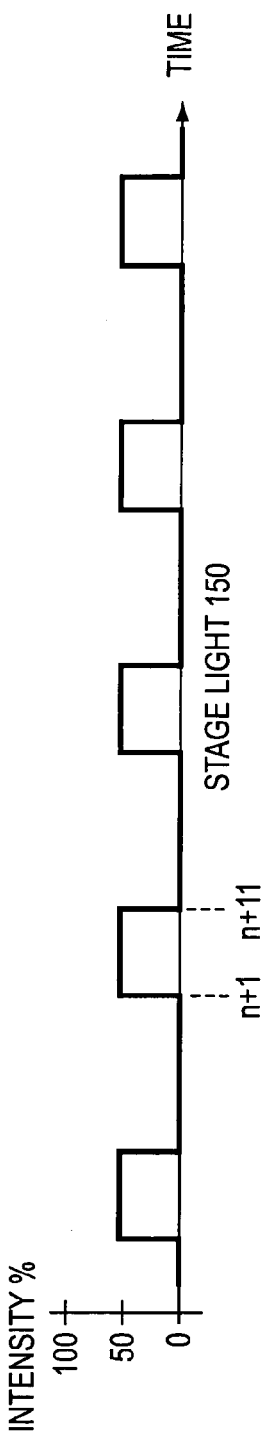

FIGS. 6–8 show an undesirable strobe lighting example where the amplitude or nominal output intensities of various light sources are adjusted in order to provide the mixture of light intensities that is required for providing a proper image. Five respective strobe instances M+1 to M+5 are shown where each of the strobes has a strobe duration period of T. Each respective strobe instance is suitable for exposure of a respective image. Assuming that the strobe illumination intensity is much greater than any background illumination intensity, the strobe duration period T establishes the effective exposure time of the related image, provided that it is shorter than the integration time of the photodetector 100.

In order to provide sufficient light required by the photodetector 100 in the shortest possible exposure time, the light intensities of all light sources are set at a highest level consistent with the light intensity mixture requirements needed to accurately measure an edge feature. For this example, the light intensity for the ring light 110 is set at 100% for the complete strobe duration period T; coaxial light 130 is set at 75% intensity and stage light 150 is set at 50% intensity. Thus, as shown in FIGS. 6–8, the light intensities of the ring, coaxial and stage lights 110, 130 and 150 are at 100%, 75% and 50%, respectively, for each of the strobe instances M+1 to M+5.

Figure 9:
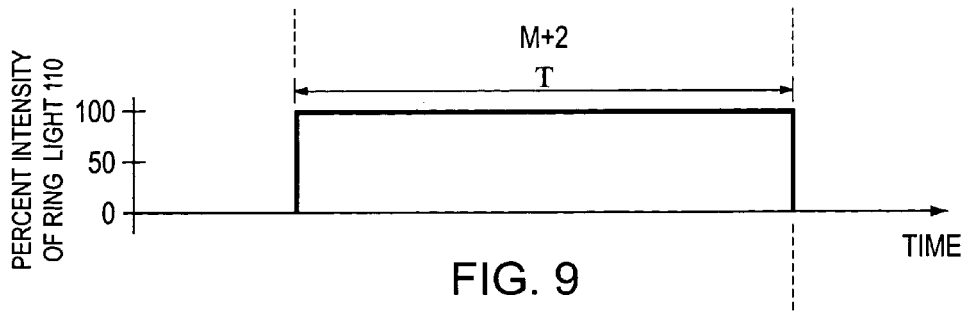
FIGS. 9–12 illustrate a technique for adjusting the relative duration of light strobe times in order to set the time-averaged light intensities of light sources relative to each other.
Figure 10:
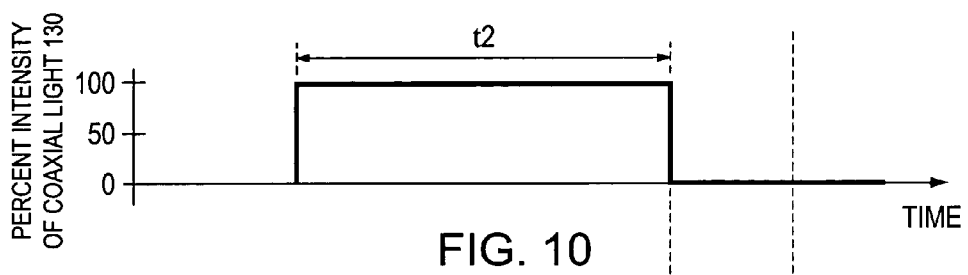
Figure 11:
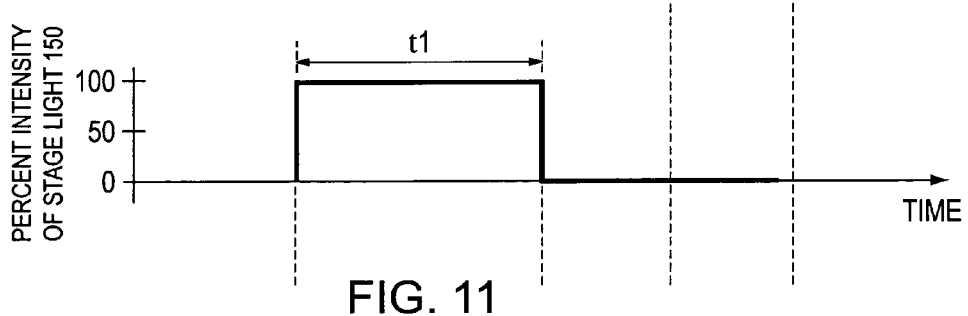

As noted previously, operating coaxial light 130 and stage light 150 at variable intensity levels presents various difficulties in controlling these lights to predictably and/or consistently produce the same frequency and intended intensity of illumination. Thus, in contrast to FIGS. 6–8, it is preferable to operate at 100% intensity, or at least at a consistent fixed intensity, and to reduce the net amount of time that the coaxial and stage lights 130 and 150 are on during the integration time of the photodetector 100 and rely on light scattering and time averaging properties of photodetector 100 to obtain the desired respective time-averaged light intensity levels in the resulting image. Thus, in the example illustrated in FIGS. 9–11, for any of the strobe instances M+1 through M+5, ring light 110 is turned on at 100% intensity for the strobe duration period T, yielding a time-averaged intensity that is 100% of its maximum time averaged intensity over the strobe duration period T; coaxial light 130 is turned on at 100% intensity for a t2 time duration that is 75% of the strobe duration period T, yielding a time-averaged intensity that is 75% of its maximum time averaged intensity over the strobe duration period T; and stage light 150 is turned on at 100% intensity for a t1 time duration that is 50% of the strobe duration period T, yielding a time-averaged intensity that is 50% of its maximum time averaged intensity over the strobe duration period T.

Figure 12:
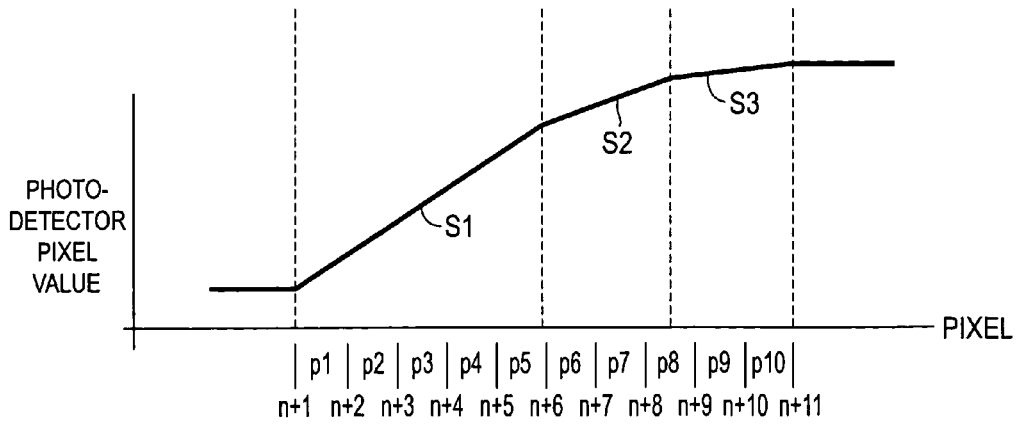

The effect that this strobing procedure has on the light accumulation values of pixels designated p1–p10 of the photodetector 100 is shown in FIG. 12. The previously described edge 144 is initially approximately at the location of the pixel p1 and moves at a constant velocity throughout the strobe duration period T, in a manner analogous to the example shown in FIGS. 3–5. Between time increments n+1 and n+6, all the light sources 110, 130 and 150 are set to 100% intensity. Thus, the pixels p1–p5 display a succession of increasing light accumulation values similar to those shown in FIG. 3. The light accumulation values linearly increase from pixel p1 to pixel p5 along a line having slope S1. After time increment n+6, the stage light 150 is turned off because, only 50% of the maximum available time-averaged light intensity from stage light 150 is desired during the strobe duration period T, in order to provide the same respective overall illumination energy, or exposure energy, as that corresponding to FIG. 8. The illumination between time increments n+6 and n+9 is supplied solely by ring light 110 and coaxial light 130 and the total light intensity reaching the photodetector 100 is less than the light intensity prior to time increment n+6. Thus, as the edge 144 sweeps across pixels p6, p7, and half of p8, the rate of light accumulation becomes less for these pixels and their respective light accumulation values approximate a line having a slope S2 which is less than S1. Coaxial light 130 is turned off just before time increment n+9 to provide 75% of the maximum available time-averaged light intensity from that light, in order to provide the same respective overall illumination energy, or exposure energy, as that corresponding to FIG. 8. Thus, the light accumulation values for pixels p9 and p10, during time increments between approximately n+9 and n+11 form a line with slope S3 that is less than S2.

Thus, while this strobing technique generally improves the controllability of light source illumination characteristics (coaxial light 130 and stage light 150), in contrast to the analogous example shown in FIGS. 3–5, pixel values of the pixels swept by edge 144 form a non-linear progression of pixel values (light accumulation values). This simple example demonstrates that, in general, when multiple light sources are strobed over unequal time periods during an image exposure, the resulting edge intensity profile will exhibit not only a blur, but also a distortion (and a corresponding edge location error) that is purely an artifact of the unequal strobe time periods. Similar to a previous discussion, even when blurring is limited to a range of less than one pixel, in a precision machine vision inspection system an image edge location will be improperly identified by the sub-pixel interpolation process due to analogous lighting-induced distortions in the relative gray level values of adjacent pixels.

In general, a workpiece will be larger than the field of view of a machine vision system. Thus, a feature coordinate or position measurement, e.g., an edge position measurement, is determined by combining a macroscopic position measurement of the stage 102 or the workpiece 140 relative to the photodetector 100 with a determination of the location of the feature within the image frame captured by the photodetector 100. The macroscopic position measurement as often provided by an encoder that monitors the relative displacement between the stage 102 and the photodetector 100. As previously noted, in many applications it is desirable to attain, as closely as possible, the same edge location measurement from a strobed image that one would obtain from an image of a workpiece that is not moving relative to the imaging system.

For example, many automated machine vision system inspection programs are created and/or verified in a training mode wherein the machine vision system is stepped through the various program steps, and the inspection images are acquired and/or verified by an operator by stopping the stage at each desired image acquisition location. In such cases, in order to provide the expected comparable measurement results, it is desirable that when the program is executed in a high speed automated mode and images are acquired with the stage moving, that nominally the same measurement results will be obtained. This can be accomplished with an improved level of accuracy when the stage velocity and the time difference between the latching of the macroscopic position value(s) of the encoder(s) and a nominal representative time for the image exposure are known.

For example, from the ideal edge example shown in FIG. 3, during the exposure time the edge was initially approximately at pixel p1 and moves uniformly during the exposure to end at approximately pixel p41. For this ideal edge example, the best estimate of the position of the edge in the image corresponding to FIG. 3 may be at the midpoint of the blurred edge intensity profile, that is, approximately at pixel p21. Assume that:

1) the midpoint pixel has an X coordinate value of Xp21;
2) the strobe duration period, that is, the time span corresponding to X Blur, is T.

This assumption is in keeping with the symbol for the strobe duration period T used with reference to FIGS. 13–16; and 3) the nominal representative time for the corresponding image exposure is the midpoint of the strobe duration period, at T/2.

If the relative position encoder value $X_e$ is latched at the beginning of the strobe duration period T, then the motion-compensated measurement coordinate of the edge may be determined to be at:

$$X = X_e + X_{p21} - (V*0.5*T) \quad (1)$$

where V is the velocity at which workpiece 140 is being moved.

In comparison to the foregoing example based on the ideal edge intensity profile shown in FIG. 2 and the corresponding blurred ideal edge intensity profile shown in FIG. 3, an actual edge intensity profile may often approximate a sigmoid shaped curve that spans a few, or several, pixels and that has a maximum slope or a maximum gradient of the sigmoid shaped curve approximately in the center of that span. Image blur may often be conveniently limited to less than a few pixels, or to a sub-pixel level. In such cases, with proper strobe illumination the resulting blurred edge intensity profile will be a sigmoid shaped curve with an extended span and a maximum slope or gradient approximately in the center of that extended span.

Many known edge detection algorithms determine edge locations at a sub-pixel level by determining the position of the largest gradient along an edge intensity profile (e.g., Sobel operator algorithms, or the like), and/or by determining the position of a gradient which exceeds a threshold value that is predefined or "learned" based on the characteristics of a reference workpiece, and that may satisfy other "learned" criteria as well. It is valid to apply Eq. (1) and its related teachings in such cases. For those cases, Eq. (1) provides an edge position measurement value that is approximately equivalent to that which would be provided with a perfectly frozen unblurred image or an image acquired with no motion.

The accuracy of the above process depends on the blurred edge intensity profile approximately maintaining the shape of the unblurred edge intensity profile, such that a gradient-based edge detection algorithm will still determine the edge location to be at approximately mid-span in the blurred image. More generally, if even more complex unblurred edge intensity profiles are maintained in the blurred image, a gradient based edge detection algorithm will tend to detect the edge approximately at the same proportional or normalized position along the length of the edge intensity profile span whether it is blurred or not. This generally requires that the extent of image blur is relatively short compared to the span of the unblurred edge intensity profile, otherwise the blur in the edge intensity profile tends toward linearity regardless of its original shape.

In such cases, with appropriate image processing the proportional position of the detected edge location along the length of the edge intensity profile span can be determined in an unblurred image obtained during the training mode mentioned above, and recorded in the automated inspection program in association with the edge measurement operations for that edge. Then, during automatic execution of the inspection program, that same proportion can be used in place of the factor 0.5 in Eq. (1) and an appropriate motion-compensated measurement result will be obtained. Of course, even if the extent of the image blur is relatively short compared to the span of the unblurred image intensity profile, an improper strobe timing relationship between various light sources can artificially distort the blurred edge intensity profile as previously demonstrated for the light sources 110, 130 and 150 in the discussion of FIGS. 9–12.

FIGS. 13–16 show a light strobe arrangement where the strobe pulses for each of the light sources 110, 130 and 150 are nominally centered about the mid-point of the overall strobe duration period T. The resulting light accumulation values for pixels p1–p10 form five line segments in which the first line segment has a slope of S3, the second line segment has a slope of S2, the third line segment has a slope of S1, the fourth line segment has a slope of S2 and the fifth line segment has a slope of S3. S1 is greater than either S2 or S3. Thus, an unblurred edge intensity profile that is a sigmoid type curve will remain a sigmoid type curve when such a strobe pulse technique is used, and using equation (1) above, and the associated teachings, will return an appropriate motion-compensated measurement result. However, more irregular edge intensity profiles will be distorted by such a strobe pulse technique, and will produce erroneous measurement results from the corresponding blurred images.

Regardless of the use of any of the foregoing techniques, because different light sources will generally show an edge at slightly different locations within an image due to differing shadowing effects, when any light source is individually turned off during an image exposure period additional edge-shifting effects will generally occur within the blurred image. Such effects will further distort the edge intensity profile and the apparent edge location.

Figure 13:
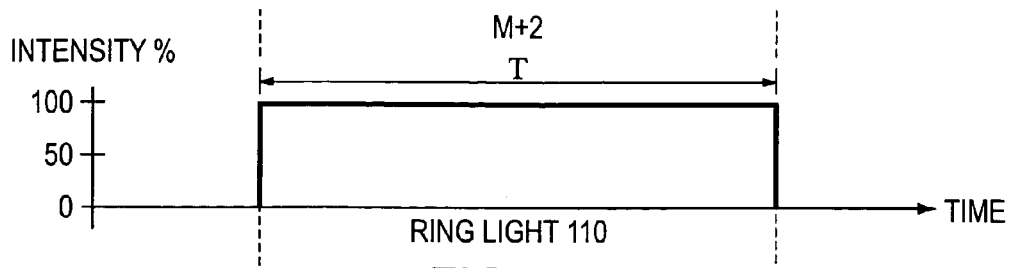
FIGS. 13–16 illustrate a technique for centering the strobe times of light sources to enhance edge detection accuracy.
Figure 14:
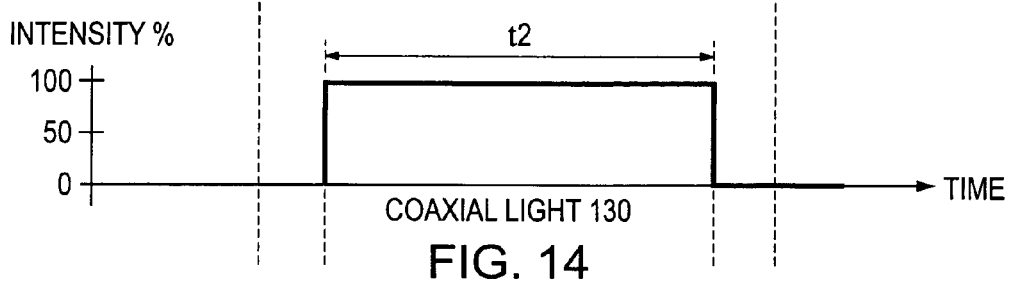
Figure 15:
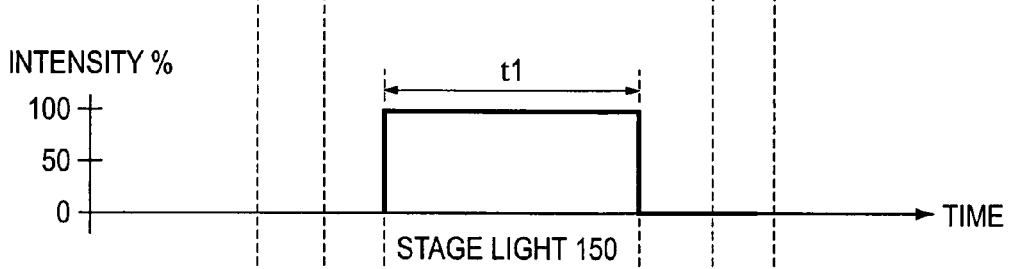
Figure 16:
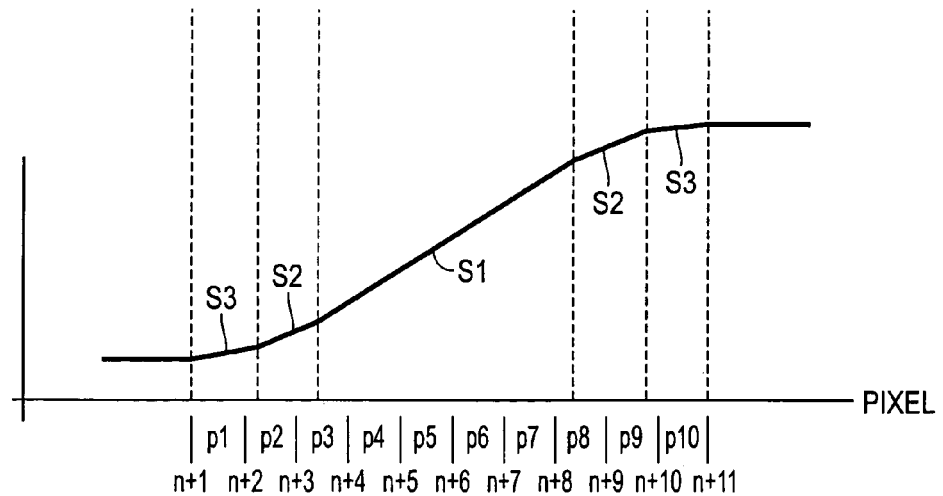
Figure 17:
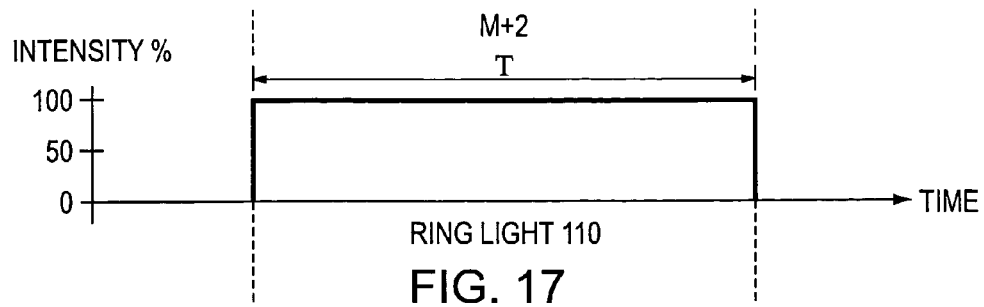
FIGS. 17–20 illustrate micro-strobing light sources to enhance edge detection accuracy.
Figure 18:
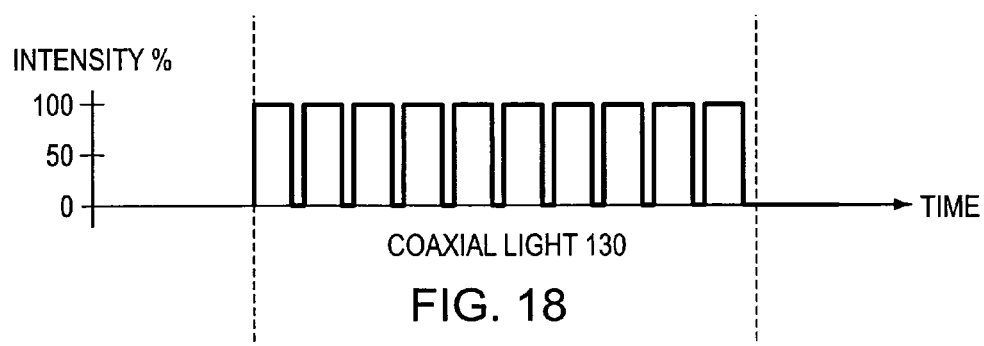
Figure 19:
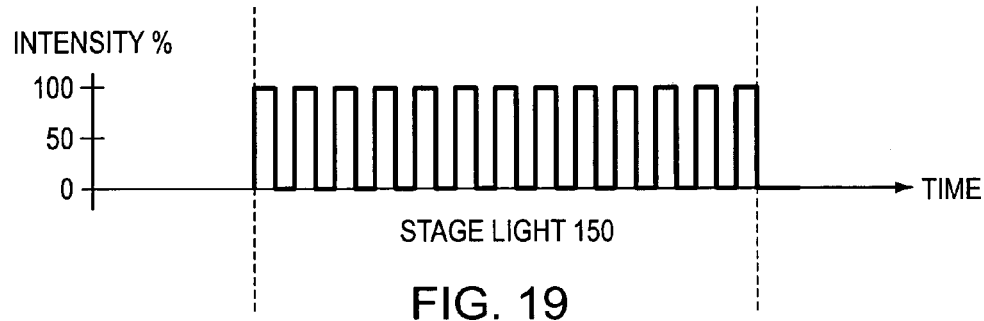

Edge location errors due to any or all of the previously described effects may be greatly reduced by micro-strobing various light sources, as demonstrated by the example shown in FIGS. 17–20, where an edge 144 is initially approximately at the location of the pixel p1 and moves at a constant velocity throughout the strobe duration period T, in a manner analogous to the example shown in FIGS. 3–5. Similar to FIG. 13, FIG. 17 shows ring light 110 being strobed at 100% intensity for the entire integration time T, yielding a time-averaged intensity that is 100% of its maximum time averaged intensity over the strobe duration period T. Instead of strobing coaxial light 130 and stage light 150 at 100% intensity but continuously for 75% and 50% of the strobe duration period time T, these lights 130, 150 are micro-strobed at 100% intensity with a duty cycle of 75% and 50%, respectively, throughout the strobe duration period time T as shown in FIGS. 18 and 19, yielding respective time-averaged intensities that are 75% and 50% of their respective maximum time averaged intensities over the strobe duration period T. Thus, coaxial light 130 and stage light 150 illuminate workpiece 140 with a consistent light pulse pattern, relatively evenly across the integration time T so that the blurred edge intensity profile remains undistorted.

Figure 20:

For example, the blurred edge intensity profile exhibited by the pixels p1–p10 forms an ideal linear progression having a slope S as shown in FIG. 20, which is the expected blurred edge intensity profile for the ideal unblurred edge intensity profile 148 shown in FIG. 2. More generally, with such a micro-strobing technique, for sigmoid type edge intensity profiles and even more complex edge intensity profiles, the shape of the unblurred edge intensity profiles are maintained in the blurred image, and a gradient based edge detection algorithm will tend to detect the edge approximately at the same proportional or normalized position along the length of the edge intensity profile span whether it is blurred or not, allowing more repeatable and accurate motion-compensated edge position measurement results, as previously described for a properly illuminated strobed image.

The frequency at which coaxial light 130 and stage light 150 are micro-strobed may be the highest frequency permitted by lighting hardware characteristics and control requirements. It is preferable that the micro-strobe frequency be set such that the time spanned by one complete on-off cycle corresponds to less than one pixel width of movement of workpiece 140. In this way, all the pixels receive an average value of light accumulation from each of the light sources 110, 130 and 150.

The above examples assume that ring light 110 is strobed at 100% intensity for the complete integration time of the photodetector 100 because it was assumed that a desired light intensity mixture required ring light 110 to have had the highest intensity for the longest period. Light intensity mixtures may vary depending on any particular workpiece and/or light source configurations. Additionally, while micro-strobing is shown above to be evenly distributed throughout the integration duration, and each light pulse of a respective light source provides the same amount of illumination energy, such distribution is not a requirement. More generally, the distribution of the micro-strobes needs only to be even enough such that a desired level of edge detection accuracy and robustness is obtained. For example, although it is not preferred, the distribution of micro-strobed pulses of a light source may be distributed throughout as little as 75% of an overall strobe duration period, and for relatively less-precise applications an adequate measure of the previously outlined benefits may still be provided. Furthermore, more generally, the respective micro-strobing light pulse pattern of each respective light source may be controlled by setting a respective micro-strobing duty cycle as previously described, by setting a respective micro-strobing repetition rate that is used in conjunction with a prescribed pulse duration, or by any other method of configuring a light pulse pattern such that provides a desired magnitude and uniformity of time-averaged light intensity and/or total illumination energy during an overall strobe duration period.

Figure 21:
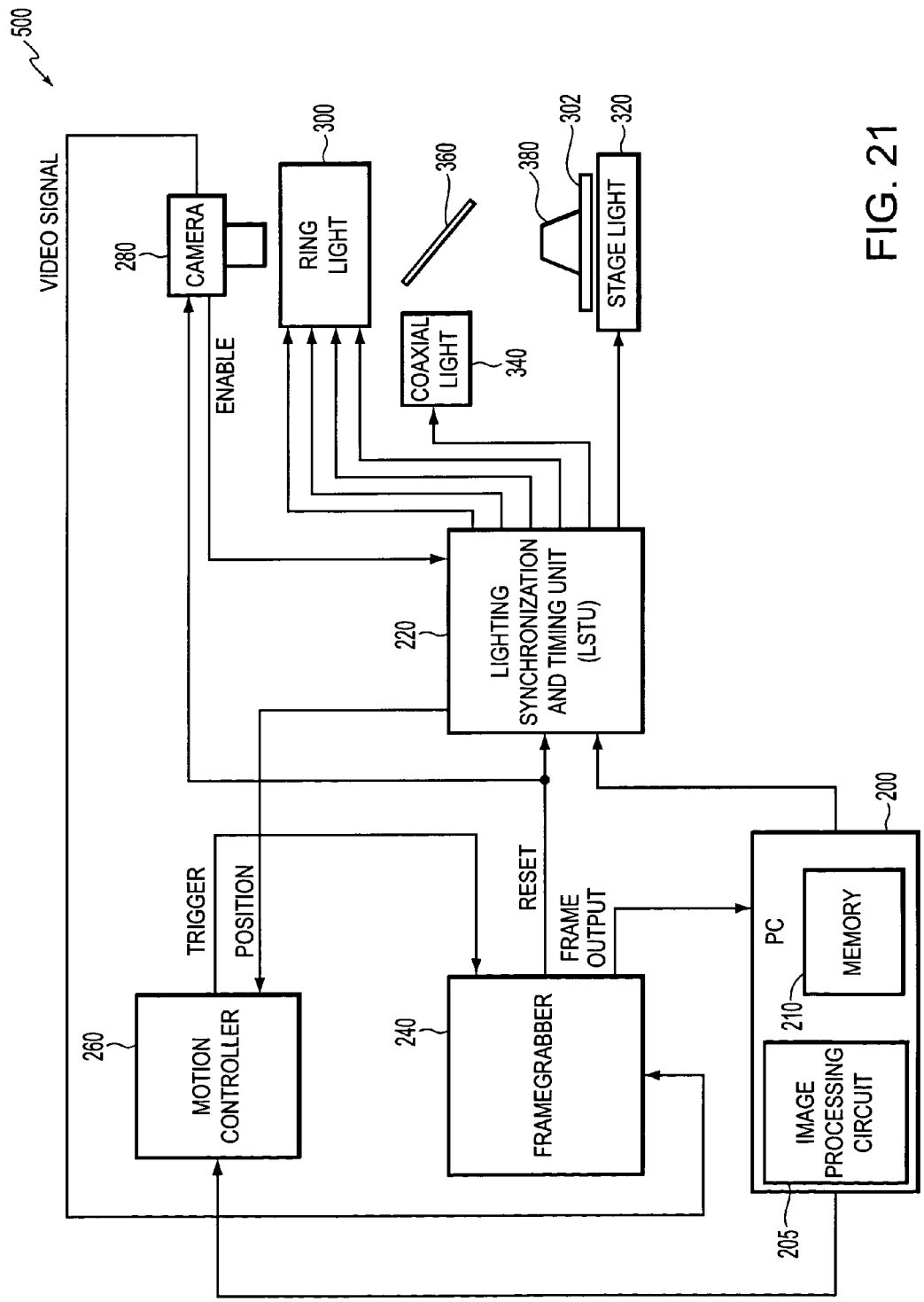
FIG. 21 illustrates an exemplary diagram of a vision system that incorporates micro-strobing.

FIG. 21 shows an exemplary system 500 (e.g., a machine vision inspection system) that incorporates the micro-strobing techniques discussed above. System 500 may include a personal computer (PC) 200, a lighting synchronization and timing unit (LSTU) 220, a framegrabber 240, a motion controller 260, a camera 280, a stage 302, a ring light 300, a stage light 320 and a coaxial light 340 with a half-silvered turning mirror 360. The ring light 300 may be formed as a combination of individually controllable sector lights. However, ring light 300 is treated as a single controlled light for ease of discussion. Workpieces such as workpiece 380 may be placed on stage 302 at specific positions. By detecting the macroscopic positions of the stage 302 and/or workpieces, the system 500 can accurately determine when to start capturing workpiece images to perform inspection operations.

An operator may input control parameters such as workpiece positions, light source intensity mixtures, etc. via a PC 200 to inspect one or more workpieces manually, semi-automatically, or automatically. An example of types of parameters that may be entered is shown in Table 1 below. Parameters such as workpiece image acquisition positions, stage velocity, magnification, integration time, effective exposure time, strobe duration period, light intensities, micro-strobing frequencies, a total number of strobe pulses per light source per workpiece image, etc., may be provided. The parameters in Table 1 are only examples, and in particular situations, more, or fewer, or different parameters may be necessary for compatibility with different equipment designs. For example, the micro-strobing frequencies may be determined by light controller hardware and set to a specific frequency based on properties of the various light sources. The control parameters may be determined by an operator who places a sample workpiece onto the stage 302 and determines the best position, magnification, lighting, etc., with which to perform the image capture to obtain optimal results. An operator may image a sample workpiece with various parameter combinations and observe the image captured by the camera 280 and assess whether the edges are properly determined. After an operable set of parameters is obtained, the operator may enter those parameter values as programmed control parameters.

TABLE 1

| | Parameter Name | | Parameter Value |
|---|---|---|---|
| 1 | Workpiece Position(s) | | X, Y, Z coordinates |
| 2 | Stage Velocity | | V |
| 3 | Strobe duration period | | 10 microseconds |
| 4 | Ring light: | % of available power or duty cycle | 100% |
| | | Pulse Frequency | 1 MHz |
| 5 | Coaxial light | % of available power or duty cycle | 75% |
| | | Pulse Frequency | 10 MHz |
| 6 | Stage Light | % of available power or duty cycle | 50% |
| | | Pulse Frequency | 25 MHz |
| 7 | Magnification | | 1× |
| 8 | Edge Position Tolerance or Allowable Blur | | +/−1.5 micron or +/−0.25 pixels |

TABLE 1-continued

| | Parameter Name | Parameter Value |
|---|---|---|
| 9 | etc. | etc. |
| | . | . |
| | . | . |
| | . | . |

The PC 200 may process the control parameters established by the operator that are obtained during the static imaging conditions of a training mode and convert them to appropriate control commands for dynamic image capture during the continuous motion conditions of an automatic inspection mode. For example, successive image acquisition locations and the associated total illumination energy to be provided by each light source may be established by the operator during a training mode and the measurement path, velocities, strobe duration period and duty cycles may then be optimized by appropriate processing and/or analysis in the PC 200, in order to yield the highest throughput, or best accuracy, etc., during automatic inspection program execution. Once the dynamic image capture control commands to be used in the automatic inspection program have been generated, the control commands (and the control parameters) may be stored in memory 210 for later retrieval and After processing the control parameters and/or retrieving control commands from memory 210, the PC 200 downloads image acquisition position parameters, the associated light control command information, and any other appropriate information to LSTU 220 and controls the other system components to execute an inspection process. In various applications it is desirable to use the dedicated processing and deterministic timing of the LSTU 220 in order to simultaneously control the high speed light pulse patterns of multiple light sources with sufficient accuracy, and at the desired position along a high-speed motion path. For example, motion controller 260 receives stage velocity information and commands stage 302 to move workpiece 380 after receiving position information from LSTU 220. LSTU 220 receives control commands from PC 200 and processes the control commands into specific data to control an image capture operation. For example, LSTU 220 may initialize controllers for light sources 300, 320 and 340, or send position information extracted from control commands to motion controller 260.

When the position parameters are received from LSTU 220, motion controller 260 begins moving the workpiece 380 and generates a trigger signal when the position of workpiece 380 reaches the specified image acquisition position. For example, when framegrabber 240 generates a reset signal that may include the integration time encoded as a pulse duration, the trigger signal from motion controller 260 is received and the framegrabber sends the reset signal to LSTU 220 and camera 280. When the reset signal is received, camera 280 initializes the photodetectors such as a CCD array by clearing any residual charges and setting the integration time, for example. After the initialization process is complete, camera 280 issues an enable signal to LSTU 220 to enable an image capture cycle.

When the enable signal is received, LSTU 220 begins micro-strobing the light sources 300, 320 and 340 for one strobe duration period during the photodetector integration time (derived from the reset signal) and cause the encoder position values from motion controller 260 to be latched at a related time. When the integration time is completed, camera 280 outputs a video signal to framegrabber 240 that receives all the pixel values from camera 280 and outputs a frame to PC 220 for processing by the image processing circuit 205, which may include the compensation of motion-induced image blur effects, for example as previously outlined. LSTU 220 then generates another position signal to motion controller 260 to start another image capture cycle. The image capture cycles are repeated until a total number of inspection image frames for each workpiece are completed and the PC 200 or the LSTU 220 issues a next position signal corresponding to a next workpiece (if any).

Figure 22:
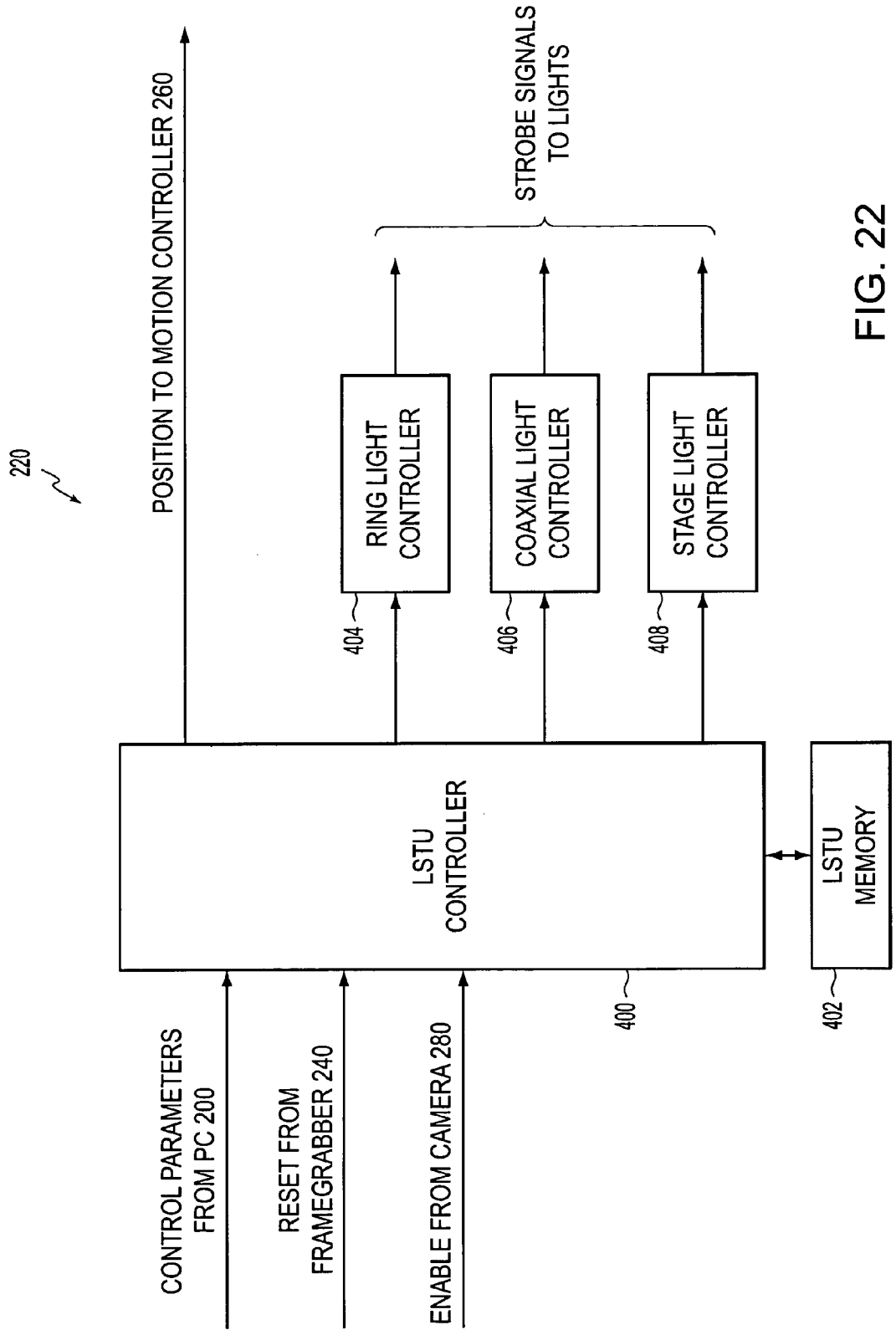
FIG. 22 illustrates an exemplary detailed diagram of a lighting synchronization and timing unit shown in FIG. 21.

FIG. 22 shows an exemplary block diagram of LSTU 220 that includes an LSTU processor/controller 400 including a high-speed clock (not shown), an LSTU memory 402 and ring, coaxial and stage light controllers 404, 406 and 408. LSTU controller 400 may be a digital signal processor, application specific integrated circuit (ASIC) or other microprocessor that performs the required processes. LSTU controller 400 receives process control parameters from PC 200 and converts these parameters into specific operation commands for each of the light controllers 404-408 and position parameters to motion controller 260.

Each of the light controllers 404, 406, and 408 may be hard wired to specific micro-strobing frequencies. If such is the case, LSTU controller 400 may output a duty cycle control signal and an on/off signal to control micro-strobing each of the light sources 300, 320 and 340. Each of the light controllers 404, 406, and 408 may be hard wired to provide specific micro-strobing pulse durations. If such is the case, LSTU controller 400 may output a repetition rate signal to control the number of micro-strobing pulses output by each of the light sources 300, 320 and 340 during an overall strobe duration period, that is, during an effective image exposure time. If light controllers 404, 406, and 408 are simple devices such as a driver, then LSTU controller 400 may generate on/off signals at the appropriate frequencies and duty cycles, etc., to directly control light sources 300, 320 and 340.

Control commands received from PC 200 may be stored by LSTU controller 400 into LSTU memory 402 for future use. LSTU memory 402 may contain many different sets of control commands loaded from PC 200 so that PC 200 may merely provide an index number to direct LSTU controller 400 to a desired set of control commands already stored in LSTU memory 402.

As indicated above, the reset signal received from framegrabber 240 may include information specifying the integration time and the LSTU controller 410 may store it in the LSTU memory 402. After receiving the reset signal from framegrabber 240, LSTU controller 400 may initialize all required light source controllers so that a micro-strobing operation may be commenced upon receipt of the enable signal from camera 280.

LSTU controller 400 extracts from the control commands position information corresponding to each of the strobes that are required. When ready to begin a next micro-strobing cycle, LSTU controller 400 sends a next position parameter to motion controller 260 for generation of the next trigger signal to commence the micro-strobing process. The control commands from PC 200 may also include a number of workpieces that should be inspected and their positions. Thus, LSTU controller 400 may store this information in LSTU memory 402 for retrieval to control the micro-strobing process.

Figure 23:
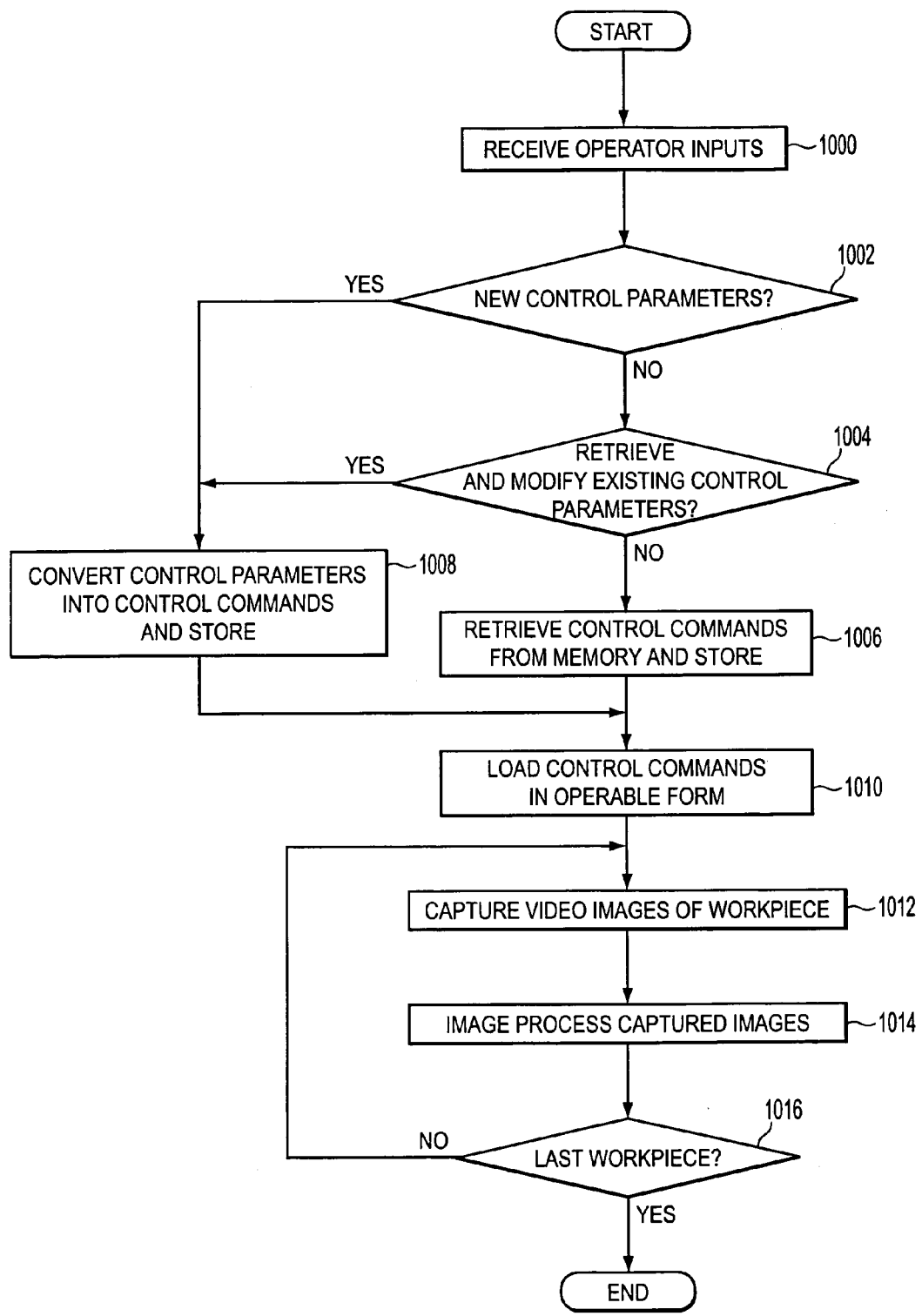
FIG. 23 is an exemplary flowchart method for creating and executing an automatic video image capture and inspection process that includes micro-strobing operations.

FIG. 23 is an exemplary flowchart of a method for creating and executing an automatic video image capture and inspection process that includes previously described micro-strobing operations. In step 1000, operator inputs are received and the process goes to 1002. In step 1002, the process determines whether the received operator inputs include completely new control parameters. If they include new control parameters, the process goes to step 1008; otherwise, the process goes to step 1004. In step 1008, the process converts the new control parameters into control commands suitable for dynamic image acquisition during automatic inspection operations.

As discussed above, control parameters entered by operators may be based on static conditions and require conversion into dynamic conditions where the workpiece is in motion. Decisions that relate to the speed at which the workpiece is moved, the number of video images or frames to be captured, the integration duration, the overall strobe duration period, the proper light intensity mixtures from available light sources, and the like may be determined, and control commands based on these decisions may be generated and stored in an operable form and sequence to perform the requested workpiece inspection. After converting the control parameters into the appropriate control commands and storing them in an operable form and sequence, the process goes to step 1010.

In step 1004, the process determines whether the operator requests to retrieve and modify existing control parameters. If modification of existing control parameters was requested, the process goes to step 1008; otherwise, the process goes to step 1006. In step 1006, the process retrieves control commands from memory, stores them in an operable form and sequence based on the operator inputs, and goes to step 1010.

In step 1010, the process loads either the newly converted control commands or control commands retrieved from memory that are stored in their operable form and sequence (for example in the form of a part program), into various operating units that perform the image capture. For example, control commands that relate to micro-strobing to achieve desired light intensity mixtures, workpiece position positions at which micro-strobing should be performed and a number of video images to be captured may be loaded into an LSTU in preparation for a sequence of image capture operations. Additionally, the integration time may be loaded into a photodetector such as a camera and the LSTU so that the photodetector and the LSTU may be synchronized in performing their operations. After control commands are loaded into the operating units, the process goes to step 1012.

In step 1012, inspection images of the workpiece are captured by using the micro-strobing technique and the process goes to step 1014. In step 1014, the captured images are image processed to identify edge features of the workpiece and determine their coordinates for inspection purposes and the process goes to step 1016. In step 1016, the process determines whether all requested workpieces (for example in a batch or tray of workpieces) have been inspected. If all workpieces have been inspected, the process goes to step 1018 and ends; otherwise, the process returns to step 1012 and is repeated for the next workpiece.

Figure 24:
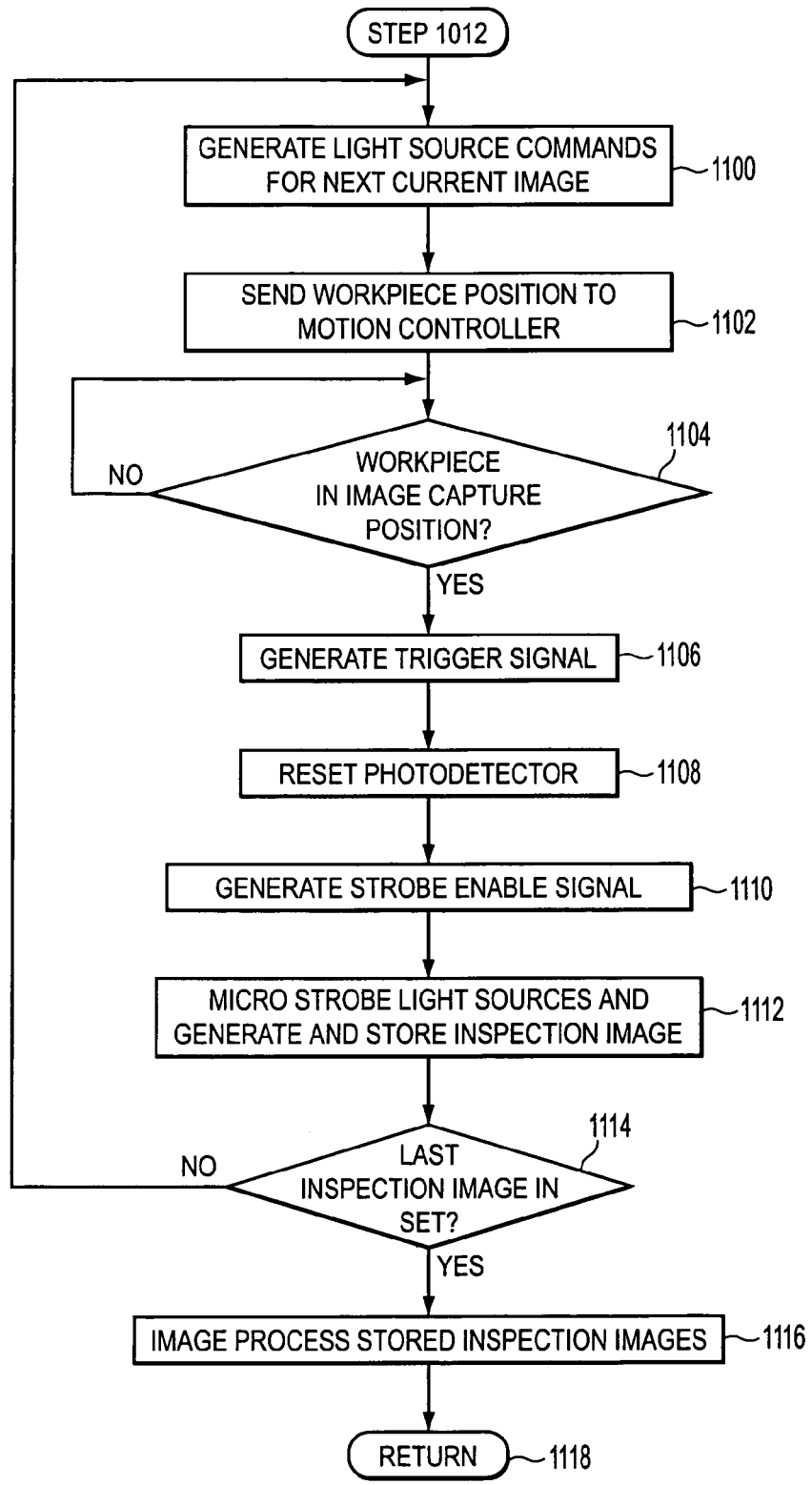
FIG. 24 is an exemplary flowchart for workpiece imaging sequence that includes a micro-strobing process.

FIG. 24 is an exemplary flowchart for a micro-strobing image acquisition process usable to capture a set of inspection images for a current workpiece. In step 1100, the process generates respective light source commands for respective light sources, for example in the form of command parameters for strobe duration period, duty cycle, and micro-strobing frequency or any other form that is operable to establish a desired micro-strobing light pulse pattern for each light source to be used for the current inspection image, and the process goes to step 1102. In step 1102, the process sends workpiece position and velocity commands to a motion controller that moves the workpiece, and the process goes to step 1104. In step 1104, the process determines whether the workpiece is positioned in the current image capture position. If it is in the current image capture position, the process goes to step 1106; otherwise, the process waits a prescribed length of time while the workpiece continues to move toward the image capture position and then returns to or repeats step 1104. In step 1106, the process generates a trigger signal to commence the image capturing process, and goes to step 1108.

In step 1108, the process resets the photodetector such as a CCD array so that all residual charges are removed in preparation for a new image capture frame. Additionally, the reset process also may communicate the integration time for the photodetector and the controller for the light sources so that the photodetector and the light source strobing controller may be synchronized for capturing a video image of the workpiece. The process then goes to step 1110. In step 1110, a strobe enable signal is generated after the photodetector is successfully reset and the process goes to step 1112. In step 1112, the light sources are micro-strobed based on the commands operable to establish a desired micro-strobing light pulse pattern for each of the light sources and an inspection image is generated and stored. The process then goes to step 1114.

In step 1114, the process determines whether all desired inspection images have been generated. If so, the process goes to step 1116; otherwise, the process returns to step 1100 to begin the image acquisition process for a new or next current image. In step 1116, the set of stored inspection images are image processed and analyzed in order to inspect the current workpiece. The image processing and analysis may include any of the various methods outlined herein for edge detection and compensating for motion-induced blur, if desired. The process then continues to step 1118. In step 1118, the process returns to the flowchart shown in FIG. 23 at step 1016.

While this invention has been described in conjunction with the exemplary embodiments outlined above, it is evident that many alternatives, modifications and variations will be apparent to those skilled in the art. The micro-strobe technique is particularly useful for precision machine vision inspection systems as described above, however, it is not so limited. The micro-strobed technique is generally useful wherever multiple illumination sources are used to image a moving object (regardless of whether the illumination sources use visible or invisible radiation) and it is desired that the positions of various image features are not distorted by the illumination technique. Such applications may include medical diagnostic imaging, high speed motion studies, or even conventional video studio imaging, for example. It is of particular use in applications using light-emitting diodes as strobed illumination sources. Accordingly, the exemplary embodiments of the invention as set forth above are intended to be illustrative only and not limiting. Various changes may be made without departing from the spirit and scope of the invention.

What is claimed is:

1. A method of strobe illumination for acquiring an image of an object, comprising:
   operating a first respective light source according to a first respective light pulse pattern including at least one light pulse while acquiring the image, the first respective light pulse pattern having an overall strobe duration period defined between a start of a first light pulse of the first light pulse pattern and an end of a last light pulse of the first light pulse pattern; and
   operating at least a second respective light source according to a second respective light pulse pattern while acquiring the image, the second respective light pulse pattern including at least one more light pulse than the first light pulse pattern, the light pulses of the second respective light pulse pattern distributed over a portion of the overall strobe duration period; wherein the respective first and second light pulse patterns at least partially govern the respective time-averaged intensities provided by the respective first and second light sources while acquiring the image.

2. The method of claim 1, wherein the portion of the overall strobe duration period is at least 75% of the strobe duration period.

3. The method of claim 1, wherein the light pulses of the second respective light pulse pattern are distributed approximately uniformly throughout the overall strobe duration period.

4. The method of claim 1, wherein for each respective light pulse pattern that includes a plurality of light pulses, each of the plurality of light pulses provides approximately the same peak intensity.

5. The method of claim 1, wherein for each respective light pulse pattern that includes a plurality of light pulses, each of the plurality of light pulses provides approximately the same amount of illumination energy.

6. The method of claim 5, wherein for each respective light pulse pattern that includes a plurality of light pulses the light pulse pattern corresponds to a respective duty cycle.

7. The method of claim 5, wherein each of the plurality of light pulses provides a predetermined amount of illumination energy and each respective light pulse pattern corresponds to a respective light pulse frequency.

8. The method of claim 1, wherein the overall strobe duration period is at most 100 microseconds.

9. A method for capturing an image of a workpiece, comprising:
   operating a first respective light source according to a first respective light pulse pattern including at least one light pulse while acquiring the image, the first respective light pulse pattern at least partially governing the respective time-averaged intensity provided by the first respective light source while acquiring the image, and the first respective light pulse pattern having an overall strobe duration period defined between a start of a first light pulse of the first light pulse pattern and an end of a last light pulse of the first light pulse pattern; and micro-strobing at least a second respective light source to provide a second respective light pulse pattern while acquiring the image, the second respective light pulse pattern including at least one more light pulse than the first light pulse pattern, the second respective light pulse pattern at least partially governing the respective time-averaged intensity provided by the second respective light source while acquiring the image; and capturing the image of the workpiece over an image integration time of a camera that overlaps the overall strobe duration period.

10. The method of claim 9, micro-strobing at least the second respective light source being substantially throughout the overall strobe duration period.

11. The method of claim 9, micro-strobing at least the second respective light source comprising:

applying one or more pulses to the second light source to drive the light source between a consistent first output level and a consistent second output level while acquiring the image, a pulse duration and a number of pulses being selected to govern the respective time-averaged intensity provided by the second respective light source, and the pulses being distributed substantially uniformly throughout the overall strobe duration period.

12. The method of claim 9, further comprising:

capturing the image of the workpiece as a set of image intensity values for a plurality of pixels while the workpiece is in motion relative to the camera; and processing the image to determine a location of at least one workpiece edge in the image based on determining a location of a image intensity value gradient that corresponds to the workpiece edge in the image.

13. The method of claim 12, further comprising:

correcting the determined location of the at least one workpiece edge based on a velocity of the motion of the workpiece during the capturing of the image.

14. The method of claim 13, wherein the correction of the determined location of the edge is based on the velocity of the motion of the workpiece V, according to $$X = X_e X_{p21} - (V*K*T)$$

where X is the corrected location of the edge, $X_e$ is a stored coordinate location of the workpiece when the image begins to be captured, $X_{p21}$ is the determined location of the edge in the image, K is a proportion that is one of a default value and a proportion determined based on an unmoving image of a corresponding edge, the proportion determined by dividing a length between a location corresponding to a start of an edge intensity profile in the unmoving image and a location of an image intensity value gradient that corresponds to the workpiece edge in the unmoving image, by an overall length of the edge intensity profile in the unmoving image, and T is the overall strobe duration period.

15. The method of claim 14, wherein K=0.5.

16. The method of claim 9, further comprising:

receiving position information for image capture of the workpiece;

moving the workpiece;

illuminating the workpiece when its position reaches a value determined based on the position information; and capturing the image of the workpiece while the workpiece is illuminated.

* * * * *